United States Patent [19]

Schmid et al.

[11] Patent Number: 5,540,770
[45] Date of Patent: Jul. 30, 1996

[54] LUSTER PIGMENTS WITH NITROGEN-CONTAINING METAL LAYERS

[75] Inventors: Raimund Schmid, Neustadt; Norbert Mronga, Dossenheim; Harald Ochmann, Dannstadt-Schauernheim; Jörg Adel, Ludwigshafen, all of Germany

[73] Assignee: BASF Aktiengesellschaft, Ludwigshafen, Germany

[21] Appl. No.: 491,483

[22] Filed: Jun. 16, 1995

[30] Foreign Application Priority Data

Jun. 23, 1994 [DE] Germany ............ 44 21 933.4

[51] Int. Cl.$^6$ ............................................. C04B 14/20
[52] U.S. Cl. .................. 106/415; 106/403; 106/404; 106/417; 106/418; 106/438; 106/439; 106/440; 106/441
[58] Field of Search ............................ 106/403, 404, 106/415, 417, 418, 438, 439, 440, 441

[56] References Cited

U.S. PATENT DOCUMENTS

| | | | |
|---|---|---|---|
| 3,087,828 | 4/1963 | Linton | 106/417 |
| 4,086,100 | 4/1978 | Esselborn et al. | 106/417 |
| 4,328,042 | 5/1982 | Ostertag et al. | 106/403 |
| 4,344,987 | 8/1982 | Ostertag et al. | 427/213 |
| 4,552,593 | 11/1985 | Ostertag | 106/417 |
| 4,618,375 | 10/1986 | Patil et al. | 106/404 |
| 4,948,631 | 8/1990 | Ostertag et al. | 427/208 |
| 4,978,394 | 12/1990 | Ostertag et al. | 106/404 |
| 5,091,010 | 2/1992 | Souma et al. | 106/403 |
| 5,246,493 | 9/1993 | Nagasaki et al. | 106/436 |
| 5,344,486 | 9/1994 | Mainz | 106/415 |
| 5,364,467 | 11/1994 | Schmid et al. | 106/404 |

FOREIGN PATENT DOCUMENTS

| | | |
|---|---|---|
| 2123783 | 6/1993 | Canada . |
| 0033457 | 8/1981 | European Pat. Off. . |
| 0045851 | 2/1982 | European Pat. Off. . |
| 0328906 | 8/1989 | European Pat. Off. . |
| 0332071 | 9/1989 | European Pat. Off. . |
| 0338428 | 10/1989 | European Pat. Off. . |
| 0353544 | 2/1990 | European Pat. Off. . |
| 0571836 | 12/1993 | European Pat. Off. . |
| 2687162 | 8/1993 | France . |
| 2522572 | 12/1976 | Germany . |
| 3237264 | 4/1984 | Germany . |
| 3534477.6 | 4/1986 | Germany . |
| 4141069 | 6/1993 | Germany . |
| 4217511 | 12/1993 | Germany . |
| 4223384 | 1/1994 | Germany . |
| WO93/12182 | 6/1993 | WIPO . |

OTHER PUBLICATIONS

Database WPI, Derwent Publications, AN–90–049655, JP–A–02 004955, Jan. 9, 1990.

*Primary Examiner*—Mark L. Bell
*Assistant Examiner*—Scott L. Hertzog
*Attorney, Agent, or Firm*—Oblon, Spivak, McClelland, Maier, & Neustadt

[57] ABSTRACT

Luster pigments based on coated plateletlike substrates comprising nitrogen-containing metal layers and if desired additionally one or more layers consisting essentially of colorless or selectively absorbing metal oxide, are prepared and used for coloring paints, inks, including printing inks, plastics, glasses, ceramic products and decorative cosmetic preparations.

7 Claims, No Drawings

LUSTER PIGMENTS WITH NITROGEN-CONTAINING METAL LAYERS

The present invention relates to novel luster pigments based on coated plateletlike substrates comprising nitrogen-containing metal layers and if desired additionally one or more layers consisting essentially of colorless or selectively absorbing metal oxide.

The present invention further relates to the production of these pigments and pigment mixtures and to their use for coloring paints, inks, including printing inks, plastics, glasses and ceramic products.

Luster or effect pigments are used in many sectors of industry, for example in automotive coatings, decorative coatings, plastics pigmentation, paints, printing inks, in particular security printing inks, and cosmetics.

Their optical effect is based on directional reflection at predominantly sheetlike, mutually parallel, metallic or strongly refractive pigment particles. Interference, reflection and absorption phenomena create angle-dependent color and lightness effects, depending on the composition of the pigment platelets.

Especially silvery luster pigments which create a metallic effect and are used in particular for coloring paints and printing inks have a large demand which cannot be satisfactorily covered by existing pigments.

DE-A-41 41 069, DE-A-42 17 511 and German Patent Applications P 43 13 541.2 and 44 05 492.0 describe metallic and silicatic pigments which are coated with metal and if desired metal oxide layers and which create a metallic effect but, in contradistinction to the typical "cold" bluish silver produced by metals such as aluminum, exhibit a "warmer" reddish silver. Furthermore, these pigments generally require an outer, protective layer to increase their corrosion resistance.

It is an object of the present invention to provide novel metallic-effect luster pigments which do not have the disadvantages mentioned and have advantageous application properties.

We have found that this object is achieved by the above-defined luster pigments.

A particularly preferred variant of the luster pigments of the present invention has A) an inner layer consisting essentially of colorless or selectively absorbing metal oxide, B) a nitrogen-containing metal layer, and C) if desired an outer layer consisting essentially of colorless or selectively absorbing metal oxide.

The present invention also provides a process for producing the luster pigments, which comprises applying to the substrate particles, or to an inner metal oxide layer already existing thereon, the nitrogen-containing metal layers by gas phase decomposition of metal carbonyls in the presence of ammonia and, if desired, the metal oxide layers in conventional manner by gas phase decomposition of volatile metal compounds in the presence of oxygen and/or water vapor or wet-chemically by hydrolysis of suitable metal compounds.

Finally, the present invention provides for the use of the luster pigments for coloring paints, inks, including printing inks, plastics, glasses, ceramic products and decorative cosmetic preparations.

The luster pigments of the present invention can have as substrates both silicatic and metallic platelets and also mixtures thereof.

Suitable silicatic substrates include in particular light-colored or white mica, especially flakes of wet-ground muscovite. It is of course also possible to use other natural micas such as phlogopite and biotite, artificial micas, talc flakes and glass flakes.

Suitable metallic substrates include all metals and alloys in platelet form known for metallic effect pigments. Examples besides steel, copper and its alloys such as brass and bronzes include in particular aluminum and its alloys such as aluminum bronze.

Preference is given to aluminum flakes which are producible in a simple manner by stamping out of aluminum foil or by widely used atomization and grinding techniques.

Suitable aluminum pigments are produced for example by the Hall process by wet grinding in white spirit. The starting material is an atomized, irregular aluminum grid which is ball-milled in white spirit and in the presence of a lubricant into plateletlike particles and subsequently classified.

Commercial products can be used. However, the surface of the aluminum particles should be substantially free of fats or other coating media. These substances can to some extent be removed by solvent treatment or better, as described in DE-A-42 23 384, by oxidative treatment.

The substrate particles used may already be coated with a first layer (A) of colorless or colored metal oxide. This is advantageous in particular when the pigments to be obtained are not to be black but are to exhibit chromatic interference colors. Suitable are the oxides customarily used for coating luster pigments, such as silicon oxide, tin oxide, zinc oxide, aluminum oxide and chromium oxide, in particular iron and zirconium dioxide, and very particularly titanium dioxide, and also mixtures thereof.

Metal oxide-coated silicatic and metallic pigments are generally known and in the case of coated mica pigments also commercially available under the names of Iriodin® (E. Merck, Darmstadt), Flonac® (Kemira Oy, Pori, Finland) and Mearlin® (Mearl Corporation, N.Y.). Metal oxide-coated mica pigments can, as will be known, be prepared from aqueous phase (DE-A-14 67 468, DE-A-25 22 572) or from the gas phase (EP-A-45 851, DE-A-32 37 264), and the corresponding metal pigments can like-wise be prepared by coating from the gas phase (EP-A-33 457) or from alcoholic solution (DE-A-35 34 477, EP-A-328 906) or from aqueous-organic phase (P 44 05 492.0).

The size of the substrate particles is not critical per se and can be adapted to their particular use. In general, the particles have average largest diameters from about 1 to 200 μm, in particular from about 5 to 100 μm, and thicknesses from generally about 0.1 to 5 μm, in particular about 0.5 μm. Their specific free surface area (BET) is generally from 0.1 to 5 m$^2$/g.

If the substrate particles are coated with a first metal oxide layer (A), the thickness of this layer is customarily within the range known for conventional luster pigments, i.e. in the case of silicate-based pigments generally from 20 to 400 nm, preferably from 35 to 250 nm, and in the case of metallic-based pigments generally from 20 to 800 nm, preferably from 70 to 600 nm.

Essential for the luster pigments of the present invention are the nitrogen-containing metal layers (B), applied directly to the uncoated substrate particles or advantageously to substrate particles already coated with metal oxide.

Layers (B) according to the present invention contain as essential constituent one or more metals, suitable being in particular those metals which form volatile carbonyls. Specific examples are vanadium, manganese, rhenium, ruthenium, osmium, rhodium and iridium, preferably tungsten, cobalt and nickel, particularly preferably chromium and molybdenum, and very particularly preferably iron.

In addition, the metal layers (B) generally contain from about 0.01 to about 22, preferably from 0.1 to about 15% by weight of nitrogen.

In general, the nitrogen will be at least partially present in the form of metal nitrides.

The nitrogen-containing metal layers (B) can advantageously be applied according to the process of the present invention by gas phase decomposition of the metal carbonyls in the presence of ammonia (chemical vapor deposition, CVD).

The dark, non-selectively absorbing layers (B) thus obtainable are notable for a uniform, homogeneous, filmlike structure. Depending on the layer thickness, they are more or less light-transmitting and also contribute to the interference.

In general, the layers (B) are from 1 to 100 nm, preferably from 0.2 to 20 nm, in thickness, especially layer thicknesses of $\leq 10$ nm giving rise to transparent or semitransparent layers which can amplify the interference color of a metal oxide-coated substrate to form particularly brilliant hues.

On coating a mica pigment already coated with a non-interference-capable layer, for example a thin titanium dioxide layer (<40 nm) with a nitrogen-containing iron layer of the present invention, a pigment is obtained with a silvery mass tone color which, in contradistinction to the iron- and $TiO_2$-coated mica pigments to be obtained by existing production processes, brings about a "colder", bluish metallic effect on application in a coating.

In addition to the advantageous color effects, the nitrogen-containing metal layers (B) are additionally notable, compared with the known pigments of the same type, for a distinct improvement in the chemical resistance, for example to oxygen (air), water and water vapor.

The luster pigments of the present invention may additionally have a top layer (C) composed of colorless or selectively absorbing metal oxides. Particularly suitable for this purpose are the metal oxides mentioned by way of example for the inner metal oxide layers (A). Depending on the method of production of these layers (e.g. wet-chemical application and drying), the metal oxide layers may still contain small amounts of water, so that the metal oxides are partly present as hydrated oxides.

The thickness of the layer (C) is not critical per se; it is generally from about 1 to 400 nm, in particular from 5 to 200 nm.

The layer (C) may confer additional protection on the pigment and also contribute to the interference of the pigment and continue the interference color series at the location determined by the substrate coated with (A) and (B). This is the case for example when zirconium oxide or titanium oxide are applied as layer (C). If, by contrast, the layer (C) consists essentially of silicon oxide, this layer will be coloristically hardly noticeable in the application medium (e.g. coatings or inks), which has a similar refractive index.

Colored metal oxides such as iron oxide and chromium oxide modify the interference color of the multilayer system through admixture of their absorption color and will with increasing layer thickness finally cover it over.

In the process for producing the novel luster pigments according to the present invention, the individual coatings are advantageously applied to the substrate particles, which may already have a first metal oxide layer, from the gas phase by decomposition of suitable starting compounds of the metals. The metal oxide layers can also be deposited wet-chemically, for example as described in German Patent Application P 44 05 492.0.

The gas phase coating is advantageously carried out in a heatable fluidized bed reactor as described for example in EP-A-45 851 by first fluidizing the substrate particles with a gas and heating them to the temperature required for decomposing the respective metal compound, generally from 100°to 600° C., preferably from 150°to 400° C. The metal compounds vaporized in an upstream vaporizer vessel using a suitable carrier gas and the gases which may be needed for the decomposition are then introduced via separate nozzles.

The novel nitrogen-containing metal layers (B) are according to the present invention applied by decomposing the metal carbonyls in the presence of ammonia.

Particularly suitable for this purpose are for example tungsten hexacarbonyl, dicobalt octacarbonyl, nickel tetracarbonyl, in particular chromium hexacarbonyl and molybdenum hexacarbonyl, and especially iron pentacarbonyl.

As generally customary for the CVD process, it is also advantageous for the production of the layers (B) for the vaporized metal compound to comprise $\leq 5\%$ by volume, preferably $\leq 2\%$ by volume, of the total amount of gas in the reactor.

The ammonia required as reaction gas can be mixed into the inert fluidizing gas (in particular nitrogen or argon) in amounts from 0.01 to 99% by volume. In the extreme case, the ammonia itself could function as the fluidizing gas; however, this is not advisable because of the waste air cleanup problems entailed. It is sensible for the fluidizing gas to have an ammonia content of generally not more than from 15 to 20% by volume; particular preference is given to an ammonia content from 0.01 to 5% by volume.

The ammonia concentration, the decomposition temperature chosen, and also the metal carbonyl used determine the amount of nitrogen incorporated in the layer (B). In general, the nitrogen content increases with increasing temperature and increasing ammonia concentration for a given metal carbonyl.

On completion of the coating and the cooling down to room temperature it is convenient to admix the fluidizing gas with a little air in order that any pyrophoric portions of the metal layer (B) may be passivated, so that the layer (B) generally also contains small amounts of oxygen.

The desired metal oxide layers (C) and also (A) can advantageously be deposited on the substrate particles, as known for example from EP-A-571 836, by oxidative decomposition of metal carbonyls or by hydrolytic decomposition of metal alkoxides. Examples of suitable volatile metal compounds are titanium and zirconium tetra-n-propoxide and tetraisopropoxide, chromium hexacarbonyl and iron pentacarbonyl.

Furthermore, to construct the metal oxide layers it is also possible, as described in German Patent Application P 44 03 678.7, for organometallics to be oxidatively decomposed. Specific examples include tin tetraalkyl, tetraalkenyls and tetraaryls and also mixed tin aryl alkyls and tin alkyl alkenyls, such as tin diallyl dibutyl, tin tetraamyl, tin tetra-n-propyl, bis(tri-n-butyltin) oxide and in particular tin tetra-n-butyl and tin tetramethyl, and zinc dialkyls, such as zinc diethyl.

The metal oxide layers can also be applied wet-chemically by hydrolysis of suitable metal compounds. This is advisable in particular for layers consisting essentially of silicon (hydrated) oxide and/or aluminum (hydrated) oxide, which can be prepared with particular advantage by the process described in German Patent Application P 44 05 492.0 by acid or preferably basic hydrolysis of organic silicon and/or aluminum compounds wherein the organic radicals are attached to the metals via oxygen atoms (ie. eg. acetyl acetonates or alkoxides, in particular $C_1$-$C_4$-alkoxides), in the presence of an organic solvent in which the metal compounds are soluble and which are miscible with water (ie. eg. alcohols, ketones, ethers, carboxamides). In a particularly preferred embodiment of this process, tetraethoxysilane and/or aluminum triisopropoxide are hydrolyzed in the presence of isopropanol and an aqueous ammonia solution as catalyst (and of course the substrate particles) and with stepwise heating to reflux temperature.

The process of the present invention can be used to produce the novel luster pigments in large amounts in a simple manner. The products are fully enrobed pigment particles obtained with high quality of the individual coatings and good hiding power and also good corrosion resistance.

If desired, the novel luster pigments based on metallic substrate particles may for deagglomeration and smoothing be subjected to an additional finishing step in the form of gentle grinding in a ball mill or comparable apparatus.

The luster pigments of the present invention are advantageously useful for many purposes, such as coloring plastics, glasses, ceramic products, decorative cosmetic preparations and in particular inks, inter alia security printing inks, and especially coatings, in particular automotive coatings, where the excellent hiding power of the pigments makes it possible to dispense with the priming otherwise necessary in the case of mica pigments. Especially the pigments with silvery hues can be used with advantage as replacement for pure (or passivated) aluminum pigments in solvent-containing and especially aqueous metallic coatings. Application by printing is possible in all customary industrial printing processes, for example screen printing, intaglio printing, bronze printing, flexographic printing and offset printing.

EXAMPLES

Preparation, application and evaluation of luster pigments according to the present invention The luster pigments of the present invention were each prepared in an externally heatable fluidized bed reactor made of glass, having a diameter of 8 cm and a height of 80 cm, and equipped with a glass frit bottom and filtersocks, suspended from the top and cleaned with a nitrogen jet, and two gas injection nozzles situated on the side above the frit bottom.

To evaluate the coloristics of the pigments obtained, in each case 0.4 g of the pigment sample was stirred into 3.6 g of a mixed polyester varnish having a solids content of 21% by weight and dispersed for 2 minutes in a Red Devil. A draw bar (wet film thickness 160 μm) was then used to prepare drawdowns of the pigmented varnishes on a piece of black and white cardboard. After the film had dried the CIELAB values were measured with a Multiflash M 45 goniospectrophotometer from Optronik (Berlin) at an angle difference of 20°, 45° and 115° to the luster angle. The reported color coordinates (L, a*, b*) relate to the standard illuminant D 65 and a viewing angle of 25°. L is the lightness, a* is the red/green content and b* the blue/yellow content. H is the hue angle [°] and C* is chroma. The measurements were carried out on single drawdowns over a black background.

To apply the pigments by bronze printing, sheets of paper were first offset printed with an unpigmented adhesive varnish (bronzing varnish) containing 95% by weight of linseed oil varnish and phenol-modified rosin ester and 5% by weight of polyvinyltoluene and then immediately transported on into the bronzing station where they were dusted with the pigment. Excess pigment powder was subsequently removed with a velvet doctor.

To apply the pigments by screen printing, 10 g of pigment were stirred into 90 g of commercially available binder solution (22.5 g of PVC copolymer Laroflex® MP45, 4.5 g of methoxypropyl acetate, 13.5 g of n-hexyldiglycol, 49.5 g of butylglycol). The screen printing ink thus prepared was applied with a commercial screen printing press (screen mesh size 112–150 μm) to coated, titanium dioxide-coated paper in a layer thickness of 45 μm and air dried.

EXAMPLES 1 to 7

600 g of the titanium dioxide-coated mica pigment indicated in each case in Table 1 were heated to T° C. under fluidization with a total of a l/h of nitrogen. 400 l/h of the fluidizing gas passed through a temperature controlled (20° C. in the case of $Fe(CO)_5$, 80° C. in the case of $Mo(CO)_6$) reservoir with × g of metal carbonyl, which was thus carried over t h into the reactor and there decomposed under the simultaneous introduction of b l/h of ammonia with the formation on the substrate particles of a filmlike deposit of nitrogen-containing metal and carbon monoxide. On completion of the metal deposition and cooling to room temperature the fluidizing gases were admixed with a little air to passivate any pyrophoric portions of the metal layer.

Details of these experiments and their results are listed in Table 1.

The coloristic data of the pigments are summarized in Table 2 (measuring angle a: 20°, b: 45°, c: 115°).

Also indicated there for comparison are the data of the comparative mica pigment C1, which represents the prior art and which was coated with iron similarly to Example 1 but in the absence of ammonia.

The standard used was a coating obtained with a finely divided aluminum powder (average particle size, BET surface area 3.5 m²/g; Alu VP 501, obtainable from Eckart, Fürth, Germany).

To evaluate the "metallic character" of the coatings obtained with the pigments of the present invention and with the comparative pigment C1, the coloristic difference from the standard is reported in terms of the ΔE values calculated according to $$\Delta E = \sqrt{\Delta H^2 + \Delta C^{*2} + \Delta L^2}$$

When color properties are virtually the same, ΔE values from 0 to 5 are likely.

The results show that the pigments of the present invention still differ from the standard, but that they are distinctly more "metallic" than the pigments obtained according to the prior art (the ΔE values are at least 10 units smaller).

TABLE 1

| Ex. | Sub-strate | a l/h $N_2$ | T [°C.] | x g Me(CO)$_x$ | t [h] | b l/h $NH_3$ | Metal content [% by weight] | N content [% by weight] based on pigment/metal layer | | Application[c] |
|---|---|---|---|---|---|---|---|---|---|---|
| 1 | X[a] | 1,800 | 200 | 218 Fe(CO)$_5$ | 10 | 5 | Fe: 9.6 | 0.36 | 3.6 | V, B, S: "cold" metallic luster |
| 2 | X | 1,600 | 220 | 450 Fe(CO)$_5$ | 24 | 10 | Fe: 15.5 | 1.03 | 6.2 | V: as Ex. 1 |
| 3 | X | 1,400 | 240 | 330 De(CO)$_5$ | 14 | 10 | Fe. 9.5 | 0.47 | 4.7 | V: as Ex. 1 |
| 4 | X | 1,600 | 250 | 290 Fe(CO)$_5$ | 8 | 15 | Fe: 10.0 | 0.36 | 3.6 | V: as Ex. 1 |
| 5 | X | 1,800 | 250 | 70 Fe(CO)$_5$ | 8 | 5 | Fe: 3.8 | 0.15 | 3.8 | V: as Ex. 1 |
| 6 | X | 1,400 | 225 | 206 Mo(CO)$_5$ | 35 | 10 | Mo: 8.5 | 0.65 | 7.1 | V: "cold" metallic luster, somewhat darker than corresponding iron-coated pigments |
| 7 | Y[b] | 1,800 | 200 | 218 Fe(CO)$_5$ | 10 | 5 | Fe: 9.0 | 0.4 | 4.2 | V: strongly violet |
| C1 | X | 1,80 | 200 | 218 Fe(CO)$_5$ | 10 | — | Fe: 9.5 | — | — | V, B, S: reddish silver |

[a]X $\triangleq$ Iriodin ® 9103 Rutile Sterling Silver WR (Merck) - silvery
[b]Y $\triangleq$ Mearlin ® Hi Lite Violet 539 X (Mearl) - violet interference color
[c]V $\triangleq$ varnish; B $\triangleq$ bronze printing, S $\triangleq$ screen printing TABLE 2a measuring angle 20°

| Ex. | H [°] | C* | V | a* | b* | ΔH | ΔC* | ΔL | Δa* | Δb* | ΔE |
|---|---|---|---|---|---|---|---|---|---|---|---|
| A1 | 253.66 | 0.54 | 123.87 | −0.15 | −0.52 | | | | | | |
| 1 | 241.91 | 3.12 | 96.40 | −1.47 | −2.76 | −0.27 | 2.59 | −27.47 | −1.32 | −2.24 | 27.59 |
| 2 | 234.93 | 2.61 | 97.55 | −1.50 | −2.13 | −0.39 | 2.07 | −26.32 | −1.35 | −1.62 | 26.40 |
| 3 | 192.75 | 1.02 | 96.61 | −1.00 | −0.23 | −0.75 | 0.49 | −27.26 | −0.85 | 0.29 | 27.27 |
| 4 | 215.13 | 1.22 | 97.62 | −0.99 | −0.70 | −0.53 | 0.68 | −26.25 | −0.84 | −0.18 | 26.26 |
| 5 | 165.37 | 1.15 | 102.09 | −1.11 | 0.29 | −1.10 | 0.61 | −21.77 | −0.96 | 0.81 | 21.81 |
| C1 | 122.87 | 1.98 | 84.01 | −1.08 | 1.66 | −1.88 | 1.44 | −39.86 | −0.92 | 2.18 | 39.93 |

TABLE 2b measuring angle 45°

| Ex. | H [°] | C* | V | a* | b* | ΔH | ΔC* | ΔL | Δa* | Δb* | ΔE |
|---|---|---|---|---|---|---|---|---|---|---|---|
| A1 | 261.39 | 1.74 | 64.54 | −0.26 | −1.72 | | | | | | |
| 1 | 252.11 | 1.84 | 12.89 | −0.57 | −1.75 | −0.24 | 0.1 | −21.65 | −0.30 | −0.03 | 21.65 |
| 2 | 248.68 | 1.59 | 45.48 | −0.58 | −1.48 | −0.37 | −0.15 | −19.06 | −0.32 | 0.24 | 19.07 |
| 3 | 106.59 | 0.64 | 44.21 | −0.18 | 0.61 | −2.06 | −1.10 | −20.33 | 0.08 | 2.33 | 20.47 |
| 4 | 4.18 | 0.17 | 44.74 | 0.17 | 0.01 | 0.84 | −1.58 | −19.80 | 0.43 | 1.73 | 19.88 |
| 5 | 106.59 | 0.64 | 44.21 | −0.18 | 0.61 | −2.06 | −1.10 | −20.33 | 0.08 | 2.33 | 20.47 |
| C1 | 114.65 | 0.51 | 30.73 | −0.21 | 0.46 | −1.81 | −1.23 | −33.82 | 0.05 | 2.19 | 33.89 |

TABLE 2c measuring angle 115°

| Ex. | H [°] | C* | V | a* | b* | ΔH | ΔC* | ΔL | Δa* | Δb* | ΔE |
|---|---|---|---|---|---|---|---|---|---|---|---|
| A1 | 2 52.36 | 1.47 | 33.64 | −0.45 | −1.41 | | | | | | |
| 1 | 273.27 | 1.60 | 23.56 | 0.09 | −1.60 | 0.56 | 0.13 | −10.08 | 0.54 | −0.19 | 10.09 |
| 2 | 261.32 | 2.45 | 23.77 | −0.37 | −2.42 | 0.30 | 0.98 | −9.87 | 0.08 | −1.02 | 9.93 |
| 3 | 268.55 | 1.96 | 21.57 | −0.05 | −1.95 | 0.48 | 0.48 | −12.07 | 0.40 | −0.55 | 12.09 |
| 4 | 331.31 | 1.09 | 24.04 | 0.96 | −0.52 | 1.61 | −0.38 | −9.60 | 1.40 | 0.88 | 9.74 |
| 5 | 292.15 | 0.86 | 24.16 | 0.32 | −0.80 | 0.77 | −0.62 | −9.48 | 0.77 | 0.61 | 9.53 |
| C1 | 264.46 | 2.35 | 12.17 | −0.23 | −2.34 | 0.39 | 0.87 | −21.47 | 0.22 | −0.93 | 21.49 |

We claim:

1. Luster pigments based on coated platelet shaped substrates comprising nitrogen-containing metal layers and if desired additionally one or more layers consisting essentially of colorless or selectively absorbing metal oxide, wherein the metal of the nitrogen-containing layer is iron, cobalt, nickel, chromium, molybdenum, tungsten, vanadium, manganese, manganese, rhenium, ruthenium, osmium, rhodium and/or iridium.

2. Luster pigments as claimed in claim 1 wherein the nitrogen is essentially present in the form of metal nitrides.

3. Luster pigments as claimed in claim 1 with
   A) an inner layer consisting essentially of colorless or selectively absorbing metal oxide,
   B) a nitrogen-containing metal layer, and
   C) if desired an outer layer consisting essentially of colorless or selectively absorbing metal oxide.

4. Luster pigments as claimed in claim 1 wherein the metal oxide layers consist essentially of titanium oxide, zirconium oxide, tin oxide, zinc oxide, silicon oxide, aluminum oxide, chromium oxide and/or iron oxide.

5. Luster pigments as claimed in claim 1 wherein the substrate comprises silicatic or metallic platelets or mixtures thereof.

6. A process for producing luster pigments as claimed in claim 1, which comprises applying to the substrate particles or to an inner metal oxide layer already existing thereon, the nitrogen-containing metal layers by gas phase decomposition of metal carbonyls in the presence of ammonia and the metal oxide layers by gas phase decomposition of volatile metal compounds in the presence oxygen and/or water vapor or wet-chemically by hydrolysis suitable metal compounds.

7. A method which comprises coloring paints, inks, plastics, glasses, ceramic products and decorative cosmetic preparations by adding thereto the luster pigments of claim 1.

* * * * *